United States Patent [19]

Sheppard

[11] 3,966,094

[45] June 29, 1976

[54] MIXING SUPPORT FOR CASTABLE MATERIAL

[76] Inventor: M. Egan Sheppard, 22 Keystone Drive, Savannah, Ga. 31406

[22] Filed: Apr. 17, 1975

[21] Appl. No.: 568,890

[52] U.S. Cl. .............................. 222/187; 118/267
[51] Int. Cl.² ..................... B67D 3/00; B05C 11/00
[58] Field of Search ................. 222/187, 188, 189; 118/267

[56] References Cited
UNITED STATES PATENTS

| | | | |
|---|---|---|---|
| 1,959,155 | 5/1934 | Campbell | 118/267 |
| 2,425,251 | 7/1947 | Landau | 118/267 |
| 2,828,715 | 4/1958 | Heyman et al. | 118/267 X |
| 3,048,537 | 8/1962 | Pall et al. | 222/189 X |

*Primary Examiner*—Allen N. Knowles
*Assistant Examiner*—Hadd Lane
*Attorney, Agent, or Firm*—Jones, Thomas & Askew

[57] ABSTRACT

Mixing support apparatus for preparing castable material such as dental porcelain or the like. The support apparatus has a porous working surface for supporting a castable material, and the working surface is disposed above a subjacent liquid reservoir which can be filled with a liquid such as water or the like. A flow of liquid is maintained from the reservoir through the porous working surface to the working surface, so that the porous working surface is constantly moistened to retard premature hardening of the castable material on the working surface.

9 Claims, 3 Drawing Figures

MIXING SUPPORT FOR CASTABLE MATERIAL

This invention relates in general to the field of ceramic casting and in particular to apparatus for supporting a mixture of castable ceramic material such as dental porcelain or the like.

The production of ceramic material is generally accomplished by mixing together one or more suitable clay substances with water to form a plastic substance which is thereafter cast, molded, or otherwise worked into a desired shape. The ceramic material hardens and dries to retain this shape, and subsequent curing or firing of the ceramic material produces a hardened cast product whose physical characteristics are determined by factors such as the chemical composition of the clay, and the time and duration of firing.

Since the workability of the ceramic material mixture during formation of the finished product is determined by the wetness of the mixture, it is important to maintain the ceramic material mixture in a desired range of wetness which allows the material to be readily worked. This is particularly important in the working of dental porcelain materials used in the preparation of false teeth, for example, inasmuch as the fit and durability of the finished product is of primary importance to the person being fitted with the teeth. It has been the practice, in the preparation of porcelain dental materials, to intermix the desired powdered porcelain material with water or another suitable liquid to provide a porcelain mixture of desired consistency. This porcelain mixture is typically supported on a work surface made of a hard and impervious material such as glass or the like, from which the technician can withdraw the material as needed.

It has been found that the porcelain mixture rapidly commences to harden or "set" because of liquid evaporation from the mix. In practice, it is frequently necessary to stir or "turn over" the porcelain mix as frequently as once each minute, possibly adding water or other liquid as necessary to maintain the mix in a desired state of plasticity. This frequent need of attention to the ceramic mix distracts the attention of the dental technician from his task of crafting the false teeth or other product, and is generally wasteful of time and effort. If the porcelain mixture is not turned over and supplied with sufficient moisture, however, the mixture rapidly becomes too hard for use and must be re-mixed by adding water.

The foregoing problems are substantially alleviated according to the present invention, which in general terms comprises a support surface which is made of porous material and which is supplied with liquid while supporting a quantity of castable ceramic material. A flow of a suitable liquid such as water or the like is maintained through the porous material to the work surface, so that a quantity of ceramic castable material disposed on the work surface can receive a supply of liquid at a relatively steady rate. The liquid supply can be provided by a liquid reservoir disposed beneath the porous material, within which is maintained a supply of liquid at a pressure sufficient to establish liquid flow through the porous material from the reservoir to the superadjacent work surface.

Other objects and advantages of the present invention will become more readily apparent from the following description of a disclosed embodiment, taken along with the drawing in which.

Figure 1:
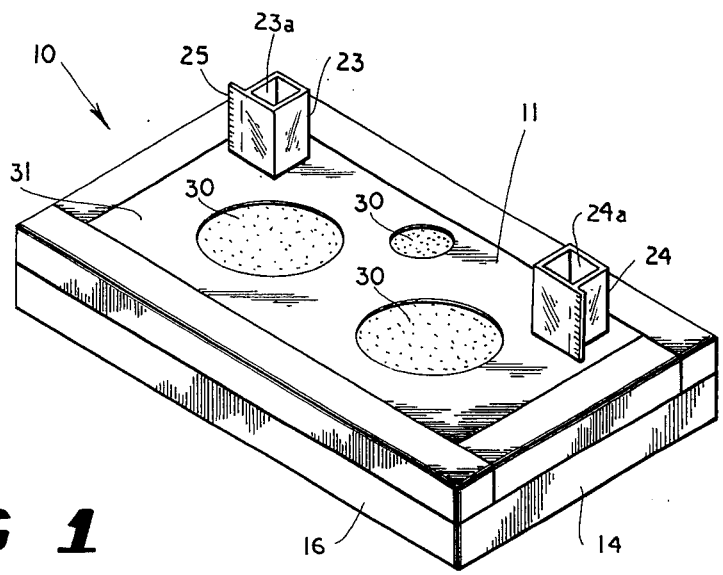
FIG. 1 shows a pictorial view of the disclosed embodiment of the present invention.
Figure 2:
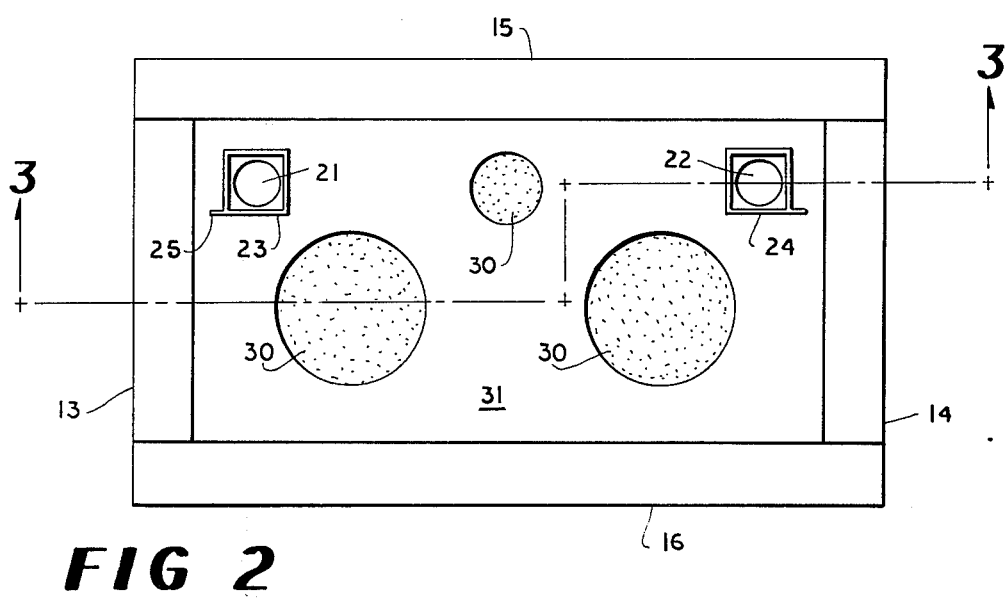
FIG. 2 shows a top plan view of the disclosed embodiment.
Figure 3:
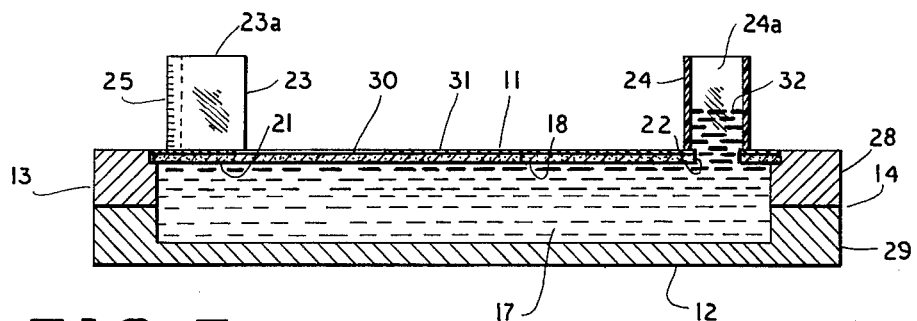
FIG. 3 shows a vertical section view taken along line 3—3 of FIG. 2.

Turning to FIG. 1, there is shown a mixing support apparatus indicated generally at 10 and having an upper wall 11 comprising a surface for mixing materials such as castable ceramics or the like. The apparatus 10 is further defined by a lower wall 12, side walls 13 and 14, a rear wall 15 (shown in FIG. 2), and a front wall 16. As best shown in FIG. 3, the upper wall 11 and the lower wall 12 are spaced apart from each other to define a reservoir 17 which is further defined in the disclosed embodiment by the two side walls 13 and 14, the front wall 16, and the rear wall 15.

Access to the reservoir 17 is provided by a pair of openings 21 and 22 formed through the upper wall 11 of the mixing support apparatus. Each of the openings 21 and 22 is surrounded by wells 23 and 24, respectively, which are secured to the upper wall 11 in liquid-tight relation and which terminate at open ends 23a, 24a a distance spaced above the upper wall. Although only a single opening 21 may be required for admitting liquid to the reservoir 17, it will be appreciated that the presence of a second opening 22 into the reservoir provides an air vent which greatly facilitates the complete filling of the reservoir with water or another desired liquid without unwanted entrapment of air within the reservoir.

Either or both of the wells 23 and 24 can be provided with a suitably-calibrated measuring scale 25 for conveniently determining the level of liquid within the well, for a purpose which will become apparent.

Since the reservoir 17 is intended to receive a quantity of liquid, all of the reservoir-defining walls except for the upper wall 11 should be constructed of a suitable non-porous material. It can be seen from FIG. 3 that the mixing apparatus is fabricated with an upper section 28 and a lower section 29 which have been suitably and preferably permanently joined together as by cementing or the like, although it will be understood that these upper and lower sections can alternatively be of unitary construction.

The upper wall 11 in the disclosed embodiment includes several regions 30 which are substantially porous to water or other liquids used in preparing ceramic mixtures of interest, with the porosity of the regions 30 extending through the thickness of the upper wall 11 into communication with the reservoir 17 within the mixing apparatus 10. The porous surface regions 30 are surrounded by a substantially non-porous area 31, although it will be understood that the entire upper surface area of the wall 11 can alternatively be a surface region of porosity in the manner of the regions designated 30. An upper wall 11 having one or more porous surface regions 30 as well as a non-porous area 31 can advantageously be provided by a porous ceramic tile which is coated with a nonporous glaze or another suitable nonporous finish throughout the desired nonporous area 31. The porous surface regions 30 are provided simply by the absence of the glaze or other nonporous surface. Alternative constructions will be within the abilities of those skilled in the art.

Considering the operation of the disclosed embodiment, it is assumed that the reservoir 17 has been filled with water or another liquid to a suitable level, as exemplified at 32 in FIG. 3, which is above the upper surface of the upper wall 11. It will be appreciated that the liquid within the reservoir 17 contacts the underside 18 of the upper wall 11 at some hydrostatic pressure which is determined by the elevation of the liquid within the wells 23 and 24. This hydrostatic pressure of the liquid in the reservoir 17 causes the liquid to flow upwardly through the upper wall 11 and to emerge at the porous surface regions 30 of the upper wall, so that the porous surface regions are moistened by the flow of liquid from the reservoir 17. The amount of liquid which flows through the upper wall 11 to the porous surface regions 30 is directly proportional to the elevation of the fill level 32 above the upper surface of the upper wall.

The ceramic mixture is prepared in the conventional manner and is disposed on one or more of the porous surface regions 30. By providing several separate porous regions 30 on the upper wall 11, a corresponding number of different ceramic materials can be separately mixed and maintained in a moistened state. In dental work, for example, several porcelain mixtures of different color shades can be maintained on the corresponding separate porous surface regions 30. The nonporous region 31 is also available, if desired, to provide a relatively hard nonporous work surface for mixing or for other purposes.

It will be understood, of course, that the foregoing relates only to a disclosed embodiment of the present invention, and that numerous changes and modifications may be made therein without departing from the spirit and the scope of the invention as defined in the following claims.

What is claimed is:

1. A mixing support for castable material, comprising:
    porous means defining a rigid porous surface region for receiving and supporting a quantity of castable material;
    means associated with said porous means to supply a mixing liquid to said porous means at a location thereon which is remote of said rigid porous surface region to establish a flow of said mixing liquid through said porous means to emerge at said rigid porous surface region, so that a mixture of castable material received on said rigid porous surface region is exposed to the emerging mixing liquid; and
    the porosity of said rigid porous surface region permitting said flow of said mixing liquid while substantially preventing said castable material from flowing into said rigid porous surface region.

2. A mixing support as in claim 1, further comprising means for supplying said liquid to said porous material at a certain pressure.

3. A mixing support as in claim 1, further comprising:
    means for supporting said porous means so that said rigid porous surface region is substantially horizontal and has an underside;
    means defining a liquid receiving reservoir which is in liquid flow communication with the underside of said rigid porous surface region; and
    means operatively associated with said reservoir to maintain the liquid therein at a desired amount of hydrostatic pressure relative to said porous means, so that a quantity of liquid from said reservoir is forced through said porous means to said rigid porous surface region.

4. A mixing support as in claim 3, wherein said liquid maintaining means comprises a liquid holding well in flow communication with said reservoir and extending upwardly to a point in elevated relation to said rigid porous surface region.

5. Mixing support apparatus for castable material, comprising:
    base means defining a liquid receiving reservoir;
    a wall supported by said base means and having a lower surface which is exposed to said reservoir;
    said wall having at least one porous region which is contiguous to said lower surface and which has a rigid porous upper surface defining a work surface for receiving a quantity of castable material;
    means in fluid flow communication with said reservoir for supplying said reservoir with a mixing liquid at a pressure which establishes liquid flow though said porous region from said reservoir to said work surface; and
    the porosity of said rigid porous upper surface permitting said mixing liquid to flow through said wall to said work surface while substantially preventing said castable material from flowing into said work surface.

6. Apparatus as in claim 5, wherein said means for supplying liquid comprises a liquid receiving well in fluid communication with said reservoir and extending upwardly to a location which is above said work surface, so that hydrostatic pressure establishes said liquid flow through said porous region when said reservoir and well are filled with liquid to a level which is above said work surface.

7. Apparatus as in claim 6, comprising a pair of said wells in fluid communication with said reservoir.

8. Apparatus as in claim 5, wherein part of said work surface of said wall is impervious to said mixing liquid.

9. Apparatus as in claim 5, wherein said wall has a plurality of said rigid porous upper surfaces, with said rigid porous upper surfaces being isolated from each other by liquid impervious means.

* * * * *